United States Patent [19]
Whittaker

[11] Patent Number: 5,765,343
[45] Date of Patent: Jun. 16, 1998

[54] INDIVIDUAL DENTAL FLOSS PACKAGING METHOD AND APPARATUS

[76] Inventor: Dale Whittaker, 7506 S. 93rd East Ave., Tulsa, Okla. 74133

[21] Appl. No.: 732,692

[22] Filed: Oct. 18, 1996

Related U.S. Application Data

[60] Provisional application No. 60/005,752 Oct. 20, 1995.
[51] Int. Cl.$^6$ ........................................ B65B 63/04
[52] U.S. Cl. ................... 53/430; 53/116; 53/450; 53/553; 53/555; 242/533.4; 242/538
[58] Field of Search ............... 53/116, 118, 430, 53/450, 553, 555, 591; 242/DIG. 3, 440, 531, 538, 548, 533.4, 533.5

[56] References Cited

U.S. PATENT DOCUMENTS

| | | | |
|---|---|---|---|
| D. 312,710 | 12/1990 | Whittaker . | |
| D. 334,249 | 3/1993 | Whittaker . | |
| 2,782,809 | 2/1957 | Smallridge | 242/440 X |
| 2,861,601 | 11/1958 | Marzolf | 242/440 X |
| 2,889,610 | 6/1959 | Buddecke | 53/591 X |
| 3,541,756 | 11/1970 | Mateski | 53/116 X |
| 3,975,883 | 8/1976 | Besnyo et al. | 53/430 X |
| 4,255,917 | 3/1981 | Stone | 53/430 |
| 4,408,726 | 10/1983 | Leonov et al. | 242/440 |
| 4,746,075 | 5/1988 | Hoxit | 242/440 X |
| 4,972,946 | 11/1990 | Whittaker . | |
| 5,121,584 | 6/1992 | Suter | 53/116 |
| 5,209,042 | 5/1993 | Rickard | 53/430 |

*Primary Examiner*—Daniel Moon
*Attorney, Agent, or Firm*—Robert R. Keegan; Head, Johnson & Kachigian

[57] ABSTRACT

There is disclosed apparatus and method for packaging individual strand segments of a strand material, such as dental floss, including apparatus for carrying out a method of supplying strand material to a rotatable guide element through a hollow shaft thereof positioned to wind the strand material around a selected mandrel of a circular array of mandrels together with controlling the moving of mandrels within and removing mandrels from within the circular path of the rotating guide element and for counting the rotations of the guide element and using that rotation count to control the advance of the array of mandrels wherein the mandrels have openings for entry of a pick-off element and are caused to be lowered to leave the coil of strand material on the pick-off element, following which the coil of strand material is urged forward by an air jet to be captured between two sheets of packaging film and transported to a stage where the packaging film sheets are sealed together around the coil to form a package in a chain of packages which then may be separated to form individual packages.

20 Claims, 8 Drawing Sheets

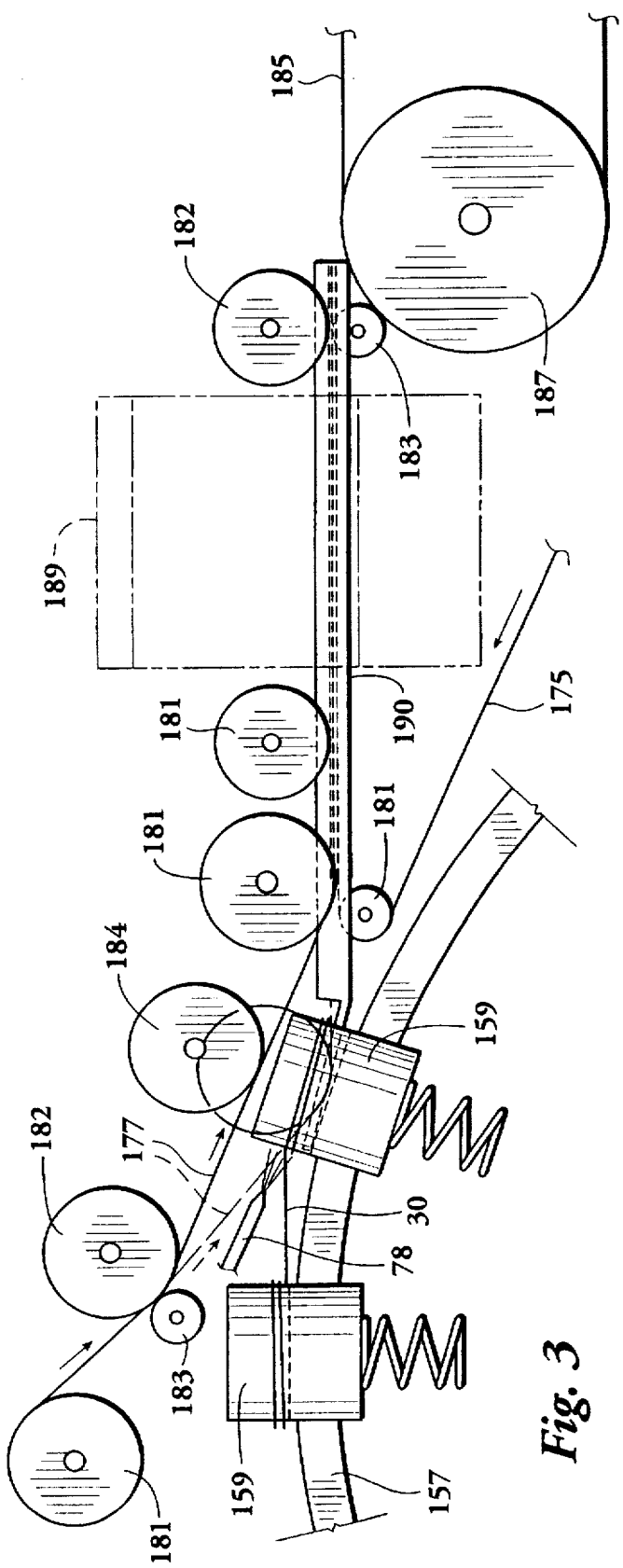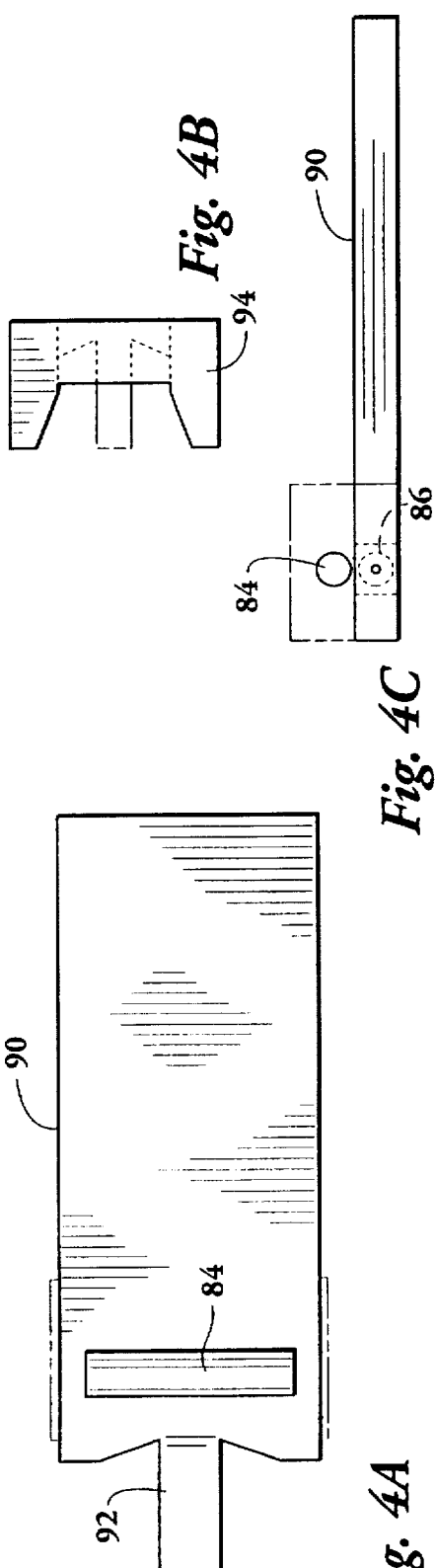

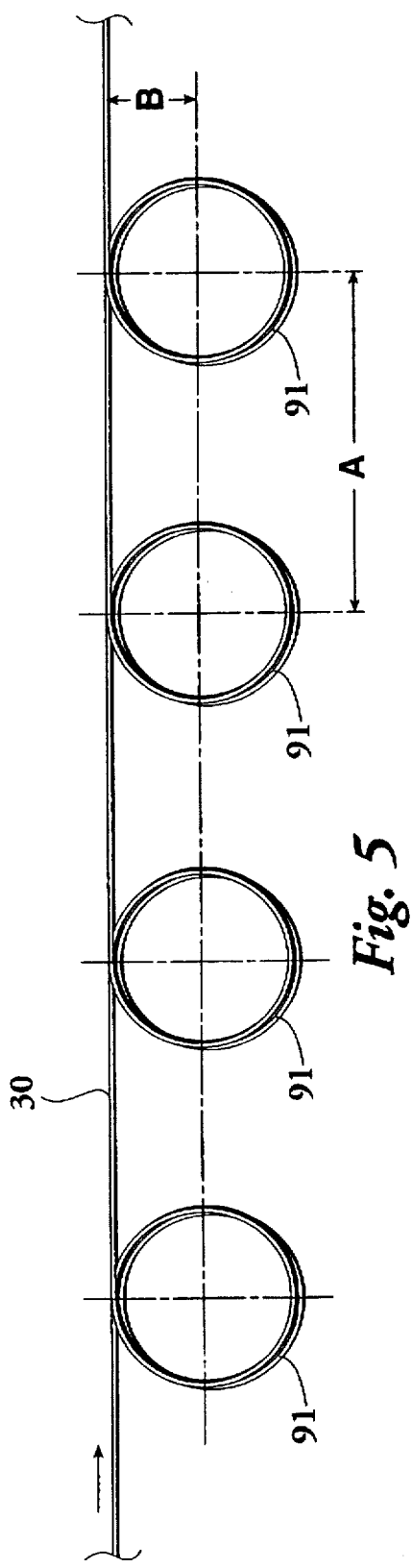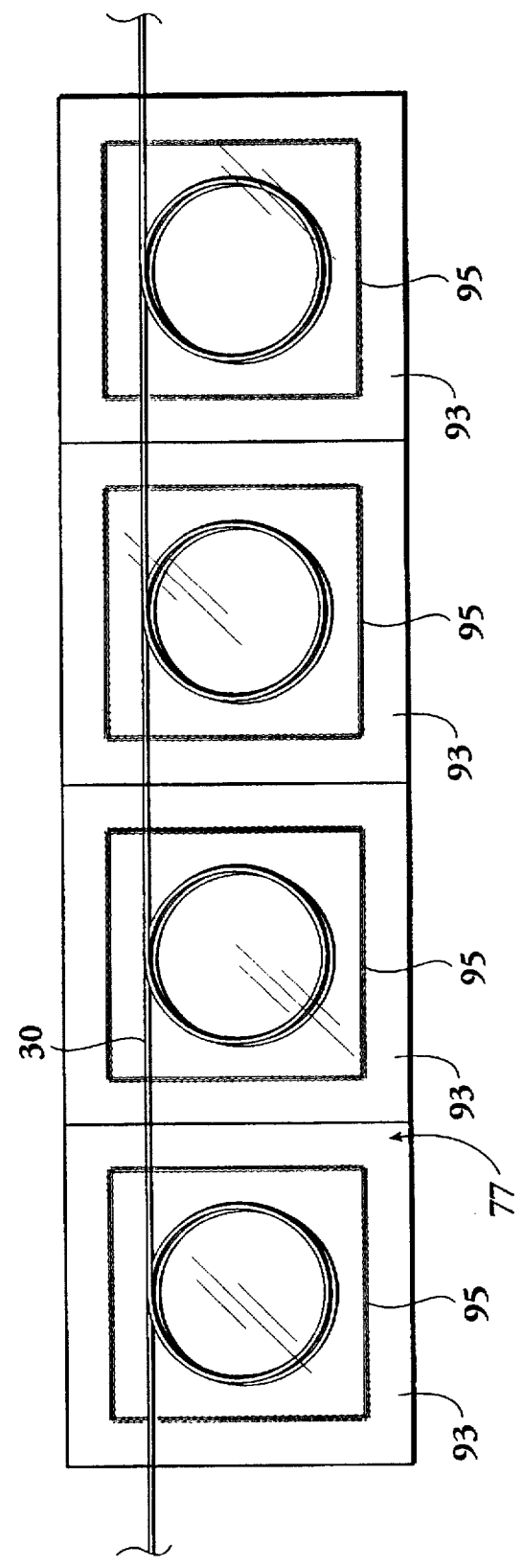

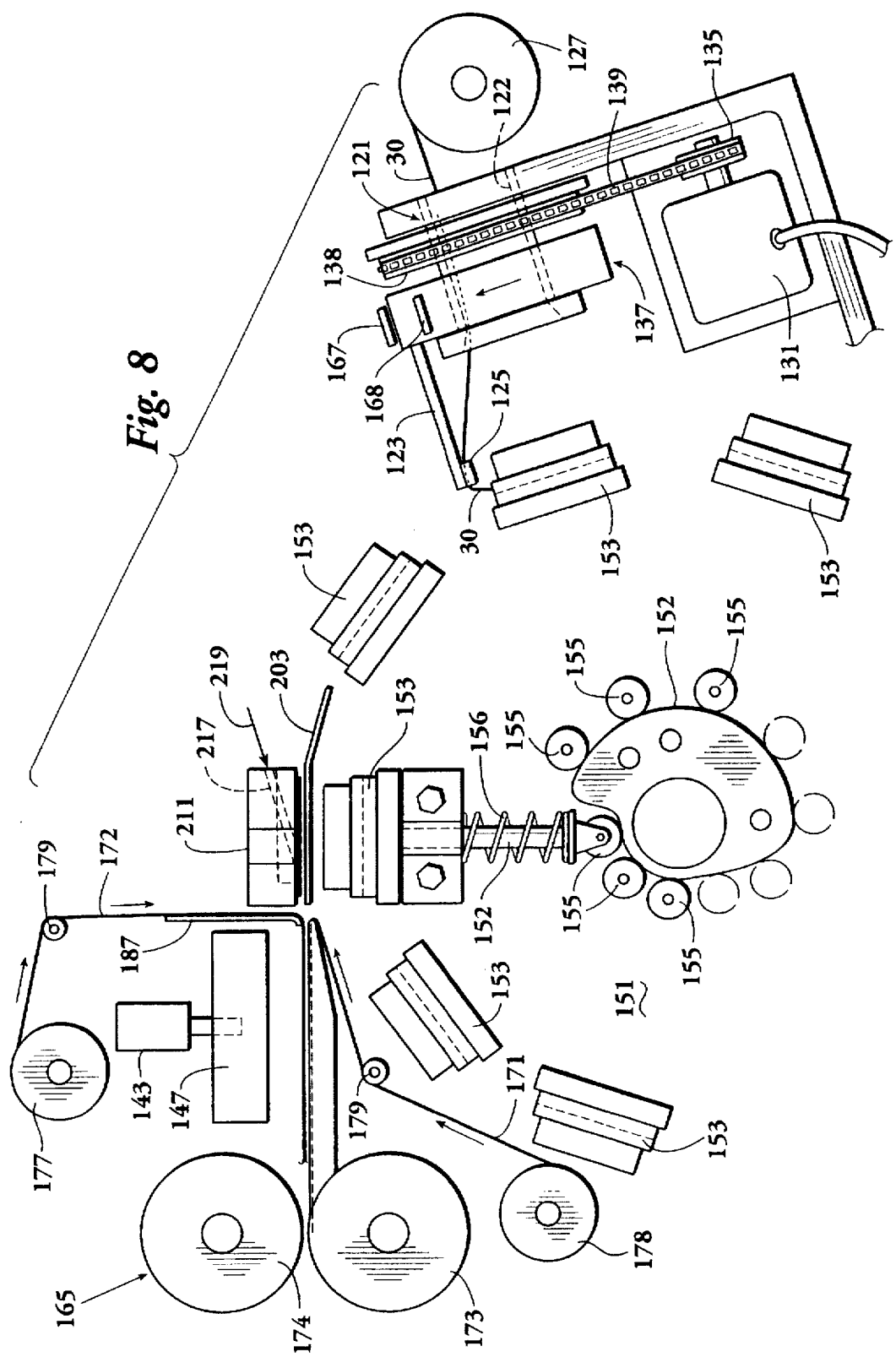

5,765,343

INDIVIDUAL DENTAL FLOSS PACKAGING METHOD AND APPARATUS

This application is a continuation of provisional application Ser. No. 60/005,752 filed on Oct. 20, 1995

BACKGROUND OF THE INVENTION

The present invention relates to methods and apparatus for producing a small individual package containing a single strand of filamentary material such as dental floss or the like coiled within a two inch square area and having a number of turns sufficient to provide a strand of at least about eighteen inches in length.

The packaging of dental floss and other filamentary material has tended to utilize a spool or some variation thereof to wind a substantial quantity of the filamentary material, typically 50 feet or more, leaving it to the ultimate user to cut off a length of the filamentary material suitable for the intended purpose. It has been recognized that in certain applications of filamentary materials, such as dental floss, it would be convenient to provide an individual package, sealed against contamination, containing a pre-cut length of the filamentary material suitable for the intended purpose. For products such as dental floss, for example, any such packaging must be produced in a very economical manner in order that it not vastly exceed the value of the product being packaged.

An example of forms of individual dental floss packaging is shown in Whittaker U.S. Pat. No. 4,972,946, issued Nov. 27, 1990 (U.S. Cl. 206/210); to a lesser extent the state of the art with respect to such packaging is exemplified in the references cited in the foregoing patent. Typical efforts at providing individual packaging for dental floss or other filamentary material involved winding a length of the filamentary material on a spindle formed of a flat piece of plastic or paperboard before placing it in the package or placing an unsupported length of filamentary material in the package in some indeterminate manner.

SUMMARY OF THE INVENTION

The packages according to the invention provide a desirable way of packaging and distributing dental floss or other filamentary material for convenience of the ultimate user. Improvements in preserving sterility or avoiding contamination will be apparent as compared with the common method of distribution by a bulk package containing a spool, reel or magazine of dental floss. Also, the individual packaging according to the invention provides the possibility of supplying the dental floss coated with solid and liquid materials, and the package can also be modified to include other dental hygiene products. If desired, the package may be formed to be opened by separating down the middle to release the coil of dental floss while the two halves of the package remain attached to the ends of the dental floss and aid in the manipulation thereof.

Particular novelty resides in the rapid and efficient method for creating the coils of dental floss in a serial fashion and then placing each of them in an individual package formed around the coil. Further novelty resides in the apparatus particularly adapted to carry out the methods of forming the packages according to the invention.

While sealed plastic film packages containing relatively short lengths of filamentary material are not new in and of themselves, some previous filament packages employ a spindle on which the filament is wound, while others insert the filament in a random, disordered manner. The present invention provides a highly efficient and effective method of forming coils of material in a serial arrangement and for incorporating each of such coils in an individually sealed plastic package with improved forms of electromechanical apparatus equipment to more readily carry out the packaging method.

BRIEF DESCRIPTION OF THE DRAWINGS

In addition to providing the advantages and fulfilling the objects described above, other advantages and features of the invention will be apparent from the following description in conjunction with the appended drawings in which:

FIG. 3 shows an alternative form of apparatus with a function similar to that shown in FIG. 2;

FIGS. 4A, 4B, and 4C show details of apparatus useful in forming and sealing coils of filamentary material in flexible plastic individual packages;

FIG. 5 is an enlarged detailed view of a series of coils of filamentary material formed according to the invention and useful in explaining the method and apparatus of the invention;

FIG. 6 shows in schematic form one of the last stages of formation of the sealed individual packages of coiled filamentary material;

FIG. 8 is a fragmentary, partially schematic side elevational view of an alternative, preferred form of packaging apparatus according to the invention;

DETAILED DESCRIPTION OF THE PREFERRED EMBODIMENTS

Figure 1:
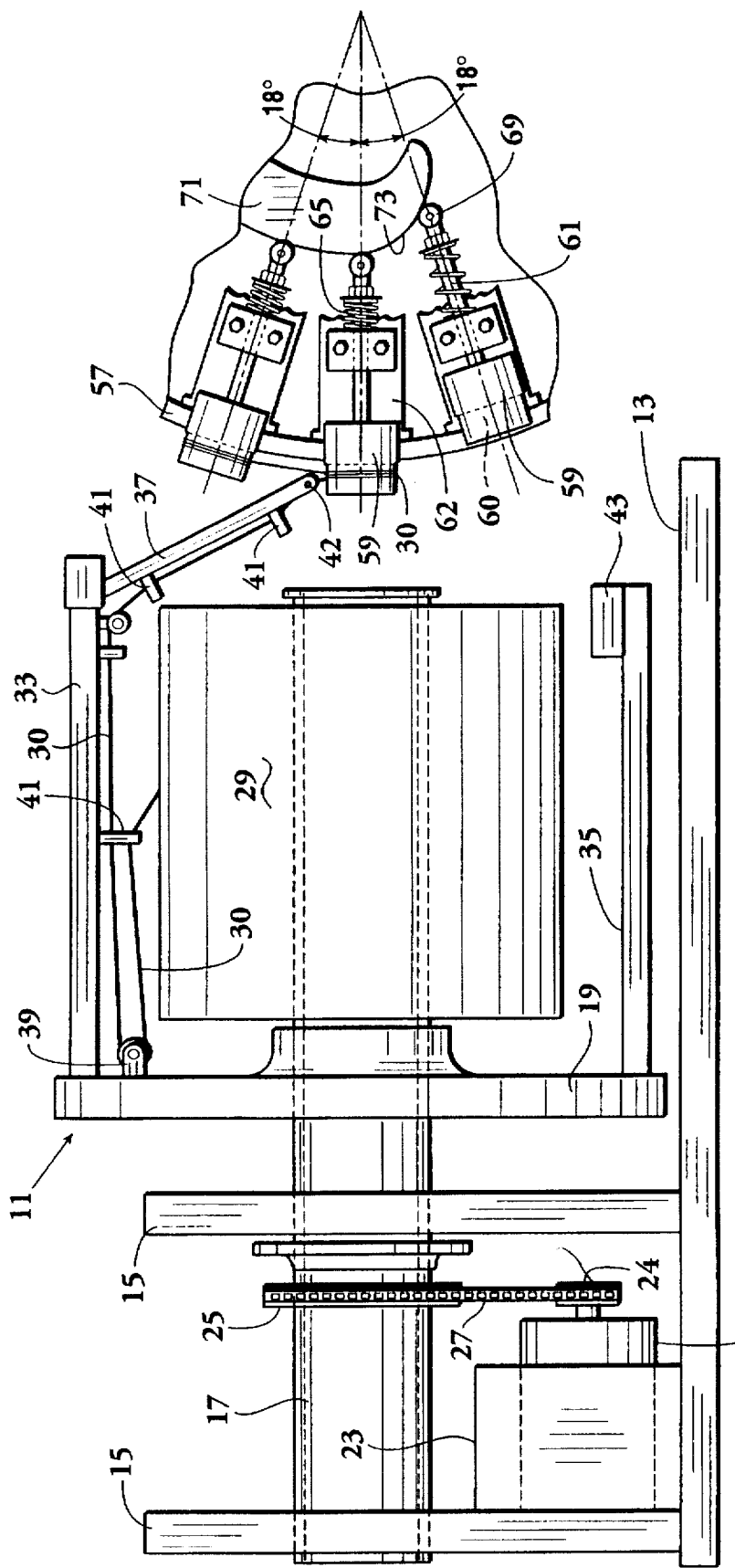
FIG. 1 shows a partially schematic side elevational fragmentary view of apparatus useful in carrying out the method of the invention.
Figure 2:
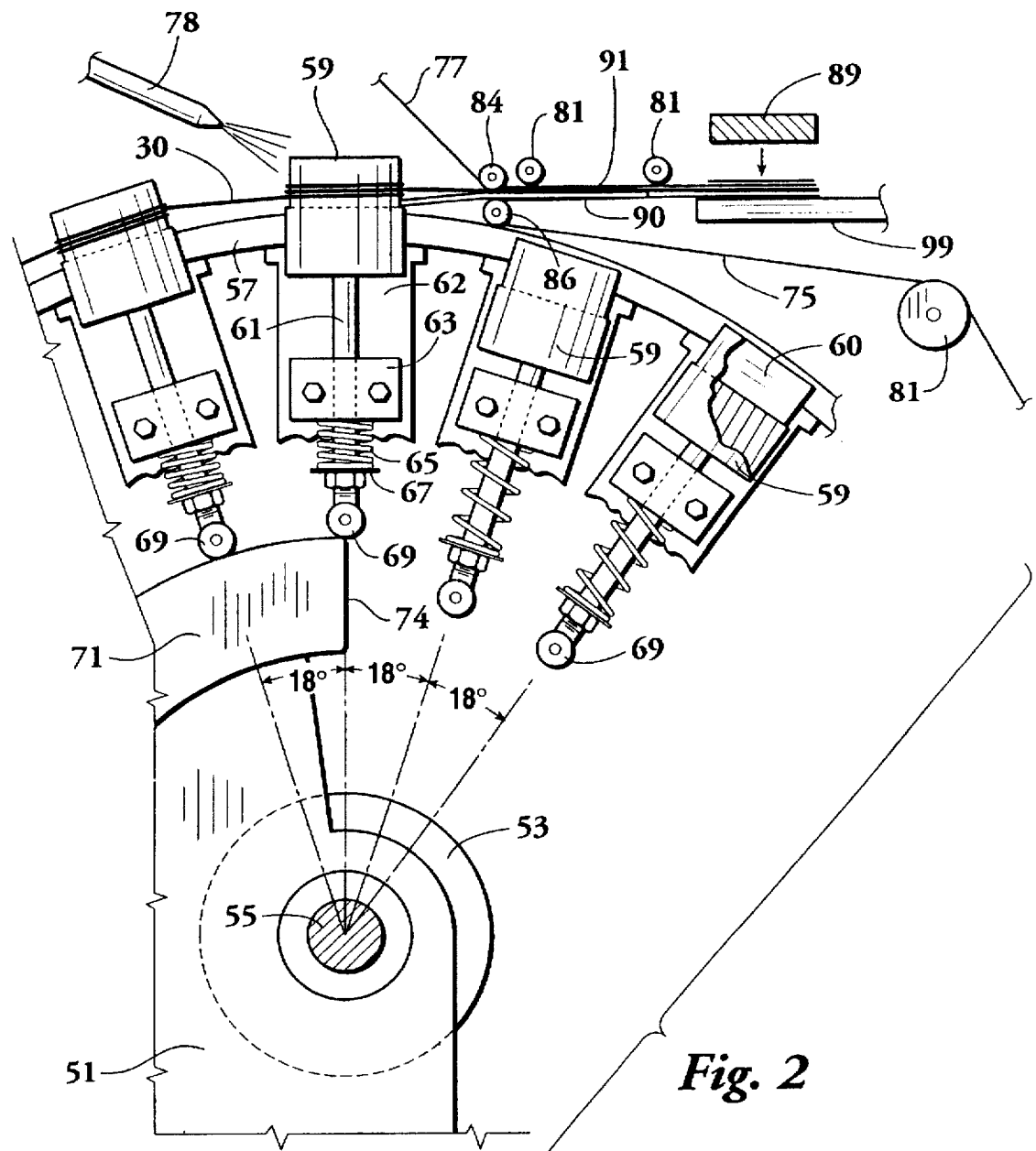
FIG. 2 shows an enlarged detailed fragmentary view of a portion of the apparatus not fully shown in FIG. 1.

Referring now to the drawings, and particularly FIG. 1 and FIG. 2, apparatus 11 is shown in FIG. 1 and FIG. 2 particularly useful and well adapted for carrying out the method of the invention to produce individual sealed packages of coiled filamentary material such as dental floss.

Apparatus such as that shown in FIGS. 1 and 2 may be employed to carry out the process of the invention in a highly automated manner so that all of the steps of sub-processes and of the complete process will be performed rapidly and in the proper sequence. It is desired to perform some or all of the following steps in an automated manner with little requirement for manual intervention by a machine operator. The necessary or desired steps are: 1) supplying a strand material to a rotating guide element or winder element, 2) causing a first of a series of mandrels to reside within a path of rotation of the guide element, 3) rotating the guide element, preferably at several rotations per second to wind turns of strand on the first mandrel, 4) moving the first mandrel out of the path of the rotating guide element of the winder and replacing it with a second mandrel of the series of mandrels, 5) removing the coiled strand portion wound on the first mandrel, preferably retaining its coiled shape, at the same time that the winder element is winding strand on a subsequent mandrel, 6) repeating steps 1 through 5 substituting the second mandrel for the first mandrel and substituting a third mandrel for the second mandrel and so on to produce a series of connected coils of strand material, 7) feeding the series of coils separated by about one diameter and connected seriatim by lengths of the strand material between two elongated sheets of plastic film material, 8) sealing together the two elongated sheets of flexible plastic material in a manner to enclose each of the coils in a separate individual container, and 9) severing the individual packages one from the other and simultaneously severing the strand of filamentary material joining the coils.

As shown in FIGS. 1 and 2 the packaging apparatus 11 according to the invention is provided with a base 13 on which are mounted two support elements 15 by which a rotatable cylinder 17 is mounted in bearings (not shown).

A winding disc 19 is fixedly mounted on cylinder 17 to rotate with cylinder 17 which is driven by motor 21 in motor mounting 23 through sprockets 24 and 25 and sprocket belt 27. Cylinder 17 accepts a dental floss supply roll 29 which is not rotatably fixed relative to cylinder 17 but tends to rotate with it absent other forces.

A timing disc on cylinder 17 allows a sensor (not shown) to read the position and velocity of winding disc 19. A cantilever arm 33 and a cantilever arm 35 are mounted on winding disc 19 for rotation therewith. Cantilever arm 33 carries a winder strut element 37 while cantilever arm 35 is provided with a suitable counterweight 43 to provide balance and minimize vibration due to the rapidly rotating structure associated with winding disc 19.

As winding disc 19 and the associated mechanism rotates the dental floss supply roll 29 rotates at nearly the same speed so that floss 30 may be fed from roll 29 through guides 41, springloaded switch 39, and through winding point 42. As dental floss 30 is drawn off the end of element 37 at winding point 42, dental floss is fed from supply roll 29 by virtue of it rotating somewhat slower than winding disc 19. Spring-loaded switch 39 serves to detect breakage in floss 30 or may be adapted to control a drag element acting on supply roll 29 to control the rate of feed of floss 30 and thereby control the tension therein.

The apparatus thus described serves to wind turns of dental floss 30 around mandrels 59 mounted on wheel 57. It should be understood that there are numerous well known forms of winding mechanisms which could be employed in whole or in part in place of the winding mechanism of FIG. 1 shown associated with winding disc 19. Therefore, the method and apparatus of the invention should not be considered to be limited to the form of winding mechanism shown by way of illustration in FIG. 1.

Referring now to FIG. 2 as well as to FIG. 1, a frame member 51 (preferably secured to and supported on base 13) supports a motor 53 having a shaft 55 on which is mounted wheel 57 carrying mandrels 59. Motor 53 is preferably a stepping motor capable of rapidly rotating wheel 57 through a predetermined fraction of a rotation; in the example shown the predetermined stepwise rotation is 18° or 1/20th of a rotation.

Also mounted on frame 51 in a fixed rather than rotatable manner is cam 71 on which cam followers 69 roll and are reciprocated by cam 71. Cam 71 extends at least about 90° around the interior of wheel 57 and is provided with a ramp 73 which moves cam followers 69 outward and a sharp dropoff 74 allowing cam followers 69 to move inward at the location of dropoff 74.

Cam followers 69 are connected to respective mandrels 59 by radial rods 61 slidably mounted in brackets 63. Rods 61 are provided with a flange 67 and a spring 65 operating between flange 67 and bracket 63 and urges each of the mandrels 59 to an inward or retracted position. Clearly, many other forms of specific apparatus could be utilized to provide for sequential extension and retraction of mandrels 59 as well known in the mechanical arts. For example, electric solenoids or fluid pressure actuators could be employed for operating the extension and retraction motion of mandrels 59 and conventional control apparatus could be utilized to actuate such mechanisms at the desired positions of rotation of wheel 57.

A conventional control system (not shown) causes the rapid step motion of wheel 57 and mandrels 59 mounted thereon to occur when cantilever arms 3 and 35 are rotated approximately 90° from the position shown in FIG. 1 thereby avoiding interference between the step motion of mandrels 59 and the winding point 42 on element 37. Any possible such interference may also be avoided by increasing the radius of the circle of motion of winding point 42, by making the mandrels oblong in shape rather than circular as shown in the drawings and/or allowing element 37 to pivot slightly during its rotational motion. Following the stepwise motion of the mandrel located coaxially with cylinder 17, the winding mechanism associated with winding disc 19 repeats the process of winding a predetermined number of turns on the next mandrel.

As best shown in FIG. 2, a mandrel 59 positioned at or near the top of the wheel will be caused to retract when its cam follower 69 reaches the dropoff 74 of cam 71. Each mandrel 59 is bifurcated by a diametrical slot 60 as indicated by dashed lines in FIG. 1 and FIG. 2 and also in a broken-away showing in FIG. 2; the slots may be from a quarter to one-half of the diameter of the mandrel 59 and may have a depth of about one-half inch or less. A receiving plate 90 for coils 91 of dental floss 30 has a tongue 92 dimensioned to fit within slots 60 thereby lifting coils 91 from mandrels 59 when they are retracted. A gentle air stream provided by air jet 78 moves coil 91 forward to be captured by an upper plastic film sheet 77 and a lower plastic film sheet 75 between rolls 84 and 86. Further rollers such as 81 transport the sandwiched interconnected dental floss coils to be sealed into rectangular enclosures by a package sealing apparatus shown schematically as heat sealer press 89 and platen 99.

Preferably rolls 81, 84 and/or 86 are operated cyclically in synchronism with the stepping of wheel 57 and mandrels 59. The distance of travel of film sheet 77 and film sheet 75 in each step cycle is no greater than the peripheral travel of wheel 57 and mandrels 59, and it may be slightly less to allow for relaxation of tension in floss 30.

FIG. 3 shows an alternative arrangement of apparatus for displacing the dental floss coil from the mandrels (partially in schematic form). Dental floss 30 having been wound on mandrels 159 in a manner similar to that previously described is retained on the mandrel until wheel 157 has rotated the mandrel 159 somewhat beyond the top position. When mandrel 159 at the top position is retracted, it is followed by a roller 184 which may either be reciprocated by a solenoid or fluid pressure actuator or may be spring urged to the position shown in dashed lines in FIG. 3. The upper packaging film 177 is fed and guided by rollers 181, 182, and 183 to pass under roller 184 so that it comes in contact with the dental floss 30 upon retraction of mandrel 159. As previously described, a gentle air stream may be used to urge the dental floss coil forward and is provided by optional air jet 78. As before, a tongue 192 on support plate 190 assures separation of the coil of dental floss 30 which is then sandwiched between upper film 177 and lower film 175. Rollers 181, 182, and 183 feed and guide the sandwiched coils of dental floss 30 through heat seal press 189 which operates to make one or more sealed enclosures surrounding a coil of dental floss in each operation of the press. The completed packages which have not yet been severed into individual units may be fed onto any suitable conveyor as indicated at 185 and 187. The packages can be severed into individual units immediately following the heat sealing step or may be transported to a separate station for any desired further processing, such as imprinting, sterilizing, or the like, and lastly being severed into individual packages.

FIGS. 4A, 4B, and 4C show an example of a support plate for use in FIG. 1 for example. Plate 90 has a tongue 92 functioning as previously described to cleanly separate the dental floss coils from the retracting mandrels while generally retaining the shape of the coils. Preferably the left edge of the plate 90 from which the tongue 92 extends has a concave shape to provide a better fit with less clearance between plate 90 and the mandrel 59 being retracted. The end of tongue 92 may be tapered to better slip under the coils. Rollers as shown at 84 and 86 form and maintain the sandwich consisting of upper film sheet 77 and lower film sheet 75 and coils of floss 30. A guide element 94 as shown in FIG. 4B may be employed to guide the coils from the position of the retracted mandrel 59 to the rolls 84 and 86.

Other forms of apparatus than that shown in FIGS. 2, 3, and 4A-4C may be employed to cleanly separate the coils from the retracting mandrels and convey it to be sandwiched between film sheets 77 and 75 and sealed into packages by press 89. For example, a belt may be provided which encircles wheel 57 and is provided with openings mating with the bifurcated top portion of mandrels 59. The belt has a periphery greater than that of wheel 57 and is provided with one or more idler pulleys so that it departs from the surface of wheel 57 at the point where the mandrels are retracted. This generally horizontal position of the belt then serves to support the coils where they are overlaid by a top film sheet and then, at a point where they leave the belt, they are sandwiched between the upper film sheet 77 and a lower film sheet 75. Such a belt arrangement could substitute for tongue 92 in providing clean separation of the dental floss coils from the mandrels and subsequently from the surface of the wheel 57.

FIGS. 5 and 6 show an example of the configuration of the coiled dental floss 30 which is formed into coils 91 of radius B; in this example A equals about one-half inch and coils 91 have a diameter of about one inch and comprise six turns of floss thereby giving a usable length of dental floss in each package of about 18 inches center to center separation of coils 91 (A in FIG. 5) is about two inches.

FIG. 6 shows the manner in which the square or rectangular seal 95 may be made around the coils 91 to permit individual packages 93 to be formed by severing the film strip midway between the coil positions. Packages 93 may be arranged to be opened by tearing in any known or conventional manner and preferably the tear line would run perpendicular to the running filament of floss 30 and midway of the package so that one-half of the torn package would be on each end of the dental floss segment when it was uncoiled.

Figure 7:
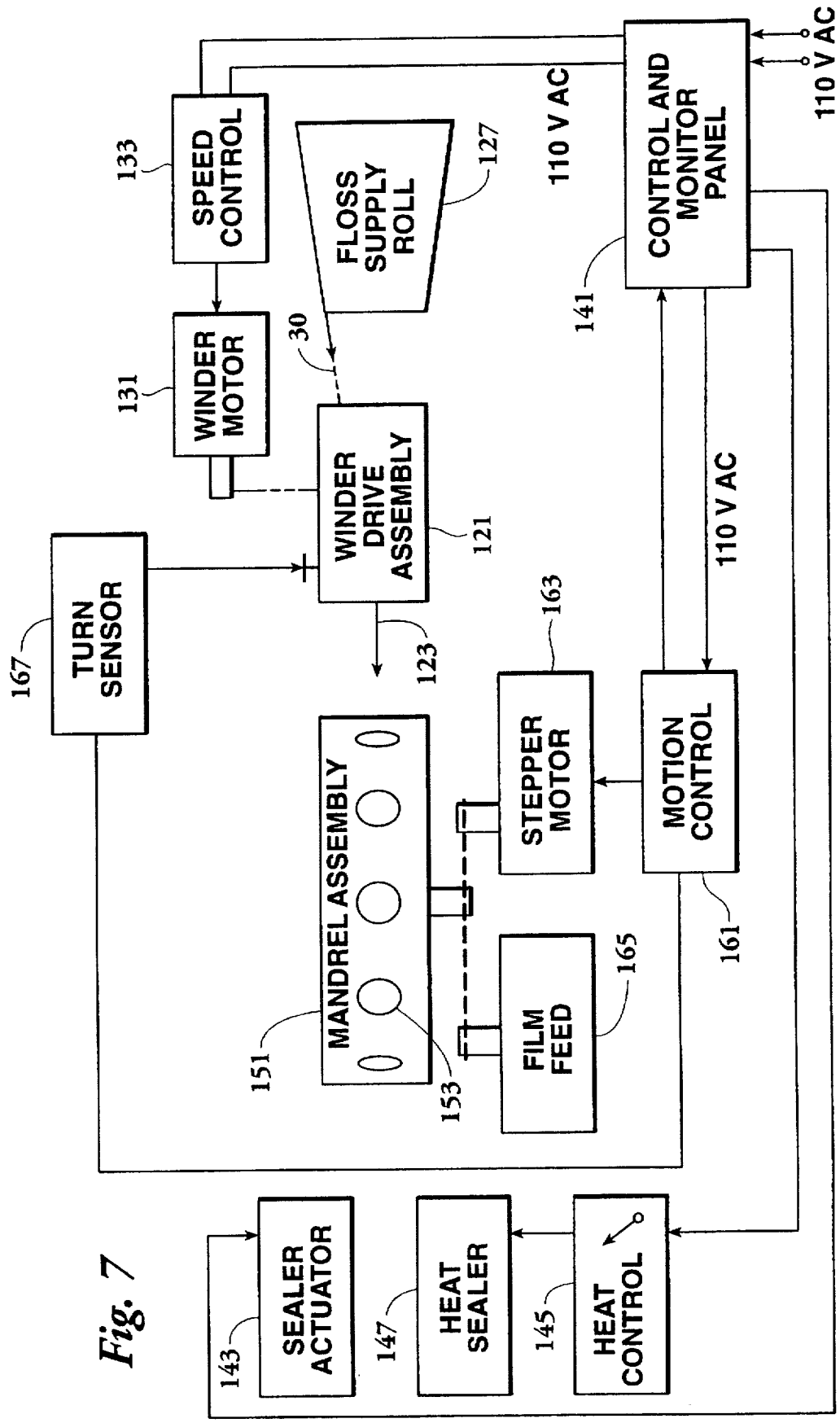
FIG. 7 is a schematic block diagram of an individual dental floss segment packaging system according to the invention.

FIG. 7 shows a schematic block diagram of the principal components of Applicant's system and their relationship together with the basic operating controls for the apparatus. While the diagram in FIG. 7 is particularly related to the preferred embodiment of apparatus to be described hereinafter, a similar control system may equally well be employed with the apparatus illustrated in FIGS. 1 through 4.

The packaging apparatus and control system designated 111 includes a winder drive assembly 121 for a rotatable winder 123 which is supplied with floss 30 from a floss supply roll 127. Preferably floss 30 is fed through a hollow shaft for rotatable winder 123 (not shown in FIG. 7).

Winder drive assembly 121 is driven by a winder motor 131 having a variable speed controllable by a speed control 133. A control and monitor panel 141 supplies power and a control signal to speed control 133.

A mandrel assembly 151 includes rotatably mountable mandrels 153 which are positionable with respect to winder 123 so that turns of dental floss may be wound thereon. A motor 163 which is preferably a stepper motor is controlled by a motion control 161 which is responsive to a turn sensor 167 providing a signal indicating the turning of winder 123 past one or more defined positions in its circular travel. Turn sensor 167 may incorporate a magnetic sensor, an optical sensor, or other conventional means for sensing the position of winder 123.

The control system for the apparatus as illustrated in FIG. 7 may be implemented with electromechanical elements such as relays, motor solenoids, and the like without employing computer control, but the apparatus may also be controlled by appropriately programmed microprocessor computer hardware.

Control and monitor panel 141 also provides power and control signals for a sealer actuator 143 which may take the form of a solenoid operated air valve and cylinder, a heat sealer 147 and a heat control 145 for heat sealer 147. For clarity and simplicity the illustrations, such as FIG. 7, do not include conventional apparatus for providing safety features and interlock apparatus for detecting and acting upon depletion of packaging film or of floss strand material, misfeeds, jams and the like. Such apparatus forms no part of the invention and conventional techniques can be employed in respect thereto.

FIG. 8 shows in partially schematic form the basic components and configuration of the preferred alternate packaging system. Floss strand 30 from floss supply roll 127 enters winder drive assembly 121 through a hollow shaft 122 and proceeds to the end of the winder 123 where it passes through an eye 125. Eye 125 may take the form of a cylinder of glass or other hard material with an opening of one-eighth to one-quarter inch. It is preferably removable and replaceable as it will be subject to abrasive wear even though formed of a hard material. Winder 123 is mounted on a cylinder 137 which may be provided with a toothed pulley 138, all of which is rotatably mounted on hollow shaft 122. Variable speed motor 131 is coupled through toothed pulley 135 to toothed pulley 138 and produces the rotary motion of cylinder 137 and winder 123. In FIG. 8, only the top one of mandrels 153 is shown in detail and other mandrels 153 are shown schematically. Floss strand 30 is wound around a mandrel 153 a predetermined number of turns selected for this example to be five turns. The diameter of mandrels about which the floss strand 30 is wound is approximately one inch and five or six turns of floss strand will provide a floss length in the finished package of from 15 to 20 inches which is the generally desired value.

Each rotation of cylinder 137 and, hence, of winder 123, is sensed by turn sensor 167 which is illustrated as a magnetic reed switch 167 responsive to a magnet 168 fixed on cylinder 137. Clearly, numerous other forms of magnetic or optical sensing devices could be employed to create one or more signals for each rotation of cylinder 137 and winder 123. Counting pulses from turn sensor 167 are counted by a suitable electromechanical or solid state counter in the monitor and control panel and utilized to control all of the functions of the packaging system. In the system illustrated by way of example, the pulse generated shortly after winder 123 passes its top position (e.g. 10° to 60°) causes initiation of the operation of stepper motor 163 to rotate the mandrel assembly by 36° (counterclockwise in FIG. 8). The speed of operation of stepper motor 163 in rotating the mandrel assembly is sufficiently fast relative to the rotational speed of winder 123 so that the mandrel 153 having just been wound with five turns and the mandrel 153 which takes its place both pass winder 123 before it reaches the lower part of its circular path where it would interfere with the arriving mandrel 153. By way of example, a rotational velocity of 400 RPM for winder 123 is compatible with a stepping motor time amounting to approximately 50 msecs (for 36° of rotation of the mandrel assembly). In other terms, one might state that rotation of the winder of as much as 90° to 120° during the transition from one mandrel to another is acceptable without causing interference between the winder and the movement of the mandrels.

An alternative, untested, control mode may provide faster rotation of the winder without interference with the mandrels in motion. In this mode, the speed of the winder would be set to and maintained at approximately one revolution during the mandrel transition time produced by the stepping motor. The rotation of the winder should, in any case, be between 270° and 480° during the mandrel transition time. Generally for this higher rotation speed mode, the position of the winder at the start of the mandrel transition would also be somewhat past (30° to 180°) the top of the winder path. In this mode winder 123 crosses the mandrels' motion path before the arrival of the next mandrel and then precedes it so that interference is avoided.

Any possible such interference may also be avoided by increasing the radius of the circle of motion of winding point 42, by making the mandrels oblong in shape rather than circular as shown in the drawings and/or allowing winder 123 to pivot slightly during its rotational motion. Following the stepwise motion of the mandrel located coaxially with winder 123, the winding mechanism associated with winding disc 11 repeats the process of winding a predetermined number of turns on the next mandrel.

Figure 10:
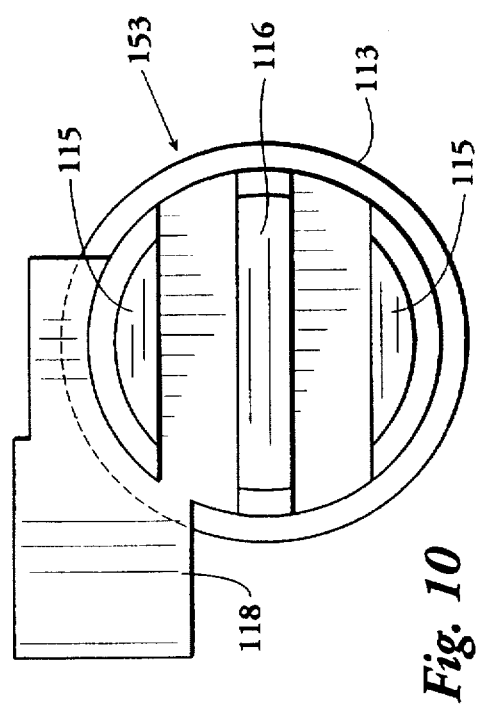
FIG. 10 is a plan view of the apparatus of FIG. 9.
Figure 9:
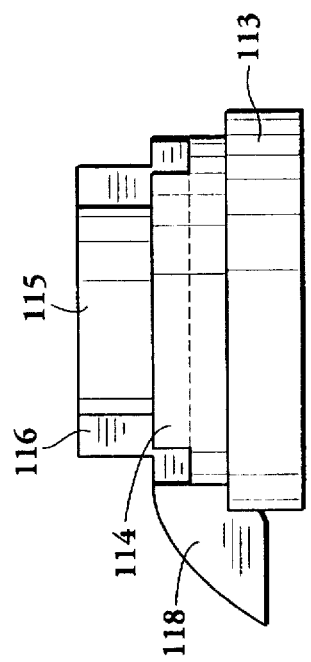
FIG. 9 is a detailed fragmentary elevational view of a mandrel subassembly from FIG. 8.

Referring now to FIGS. 9 and 10 in addition to FIG. 8, as one of the mandrels 153 approaches the topmost position it encounters pick-off element 201 having a bifurcated or double tongue portion 203, (see FIG. 13) and pick-off element 201 is preferably formed of a resilient plastic material. Each of the tongue portions 203 is inserted into mandrel 153 as it approaches the top position in the opening between center wall 116 and outer wall 115 of the mandrel 153, see FIGS. 9 and 10. The ends of tongue portions 203 are bent slightly downward to better conform with the direction of motion of the mandrels 153. Tongue portions 203 insert themselves below the ridge formed at the top of mid-portion 114 of mandrel 153 and hence insert themselves below the floss strand wound on mandrel 153. Floss strand is caused to be wound above mid-portion 114 in part by the action of lip 118 best shown in FIGS. 9 and 10. Lip 118 is provided with a smoothly curved portion at its extremity which intercepts any strand of floss tending to be wound below the top of mid-portion 114 of mandrel 153 and lifts it to the desired position. Lip 118 also provides a support for the leading segment of a strand of floss running from a trailing mandrel to the mandrel in front of it. This prevents any tendency of the floss strand to sag between mandrels to the extent that it would interfere with operation of the system. It should be pointed out, however, that lip 118 is an optional feature of the mandrel configuration which, in some cases, may not be necessary. As mandrel 153 approaches the top position it reaches a point where it is no longer maintained at its upper position by cam 152 as the cam follower 155 associated therewith drops to the lower level of cam 152. This action is accelerated by spring 156 acting on rod 52 drawing the mandrel 153 down to a position near its mounting bracket 154. This occurs only shortly after tongue portions 203 have fully penetrated the mandrel 153 so that they support the coil of floss strand being lifted from mandrel 153. A top plate 211 has cutouts 215 which accommodate outer walls 115 of a mandrel and a center cutout which accommodates center wall 116 of a mandrel as it approaches the top position and is about to drop to its lower level. At this point the coil of floss strand is essentially enclosed by tongue portions 203 of pick-off element 201 below the coil and by top plate 211 above the coil while the mandrel is withdrawing itself from within the coil.

While the coil is essentially restrained on all sides, it is, nevertheless, free to move forward upon the initiation of the next mandrel advance cycle and this transmissional motion of the coil is caused by an air jet provided through passages 217 in top plate 211. For simplicity and clarity the air supply apparatus and the necessary tubing is not shown in detail and is indicated schematically by the arrow 219.

Just forward of the top position for mandrels 153 a lower packaging film strip 171 and an upper packaging film strip 172 are brought together from supply roll for film 177 and supply roll for film 178 which are shown only schematically as they would be very large rolls positioned at some distance from the mandrel assembly 151. Conventional tension control apparatus and idler rollers would be arranged in a known manner to provide the film strips at the proper tension in proximity to the top position for mandrels 153. This apparatus is indicated only schematically by idler rollers 179.

Packaging film strips 171 and 172 are guided to a position of parallelism and close proximity by curved low frictions surfaces at the lower end of heat shield 187 and the rounded end of film support 175.

Film feed 165 for the apparatus of FIG. 8 is shown schematically therein indicated by lower roll 173 and upper roll 174. The stepper motor 163 which drives the mandrel assembly 151 also drives rolls 173 and 174 of film feed 165 through an appropriate positive drive device such as a toothed belt and pulley arrangement or the like. The rotational speed ratios for rolls 173 and 174 (which are preferably geared together to run at the same speed) and the relative speed of the mandrel assembly 151 is determined in such a way that the peripheral speed of rolls 173 and 174 is equal to or slightly less than the peripheral speed of the mandrel assembly at the radius of the floss coil positions. The slightly lesser peripheral speed for rolls 173 and 174 allows for relaxation of tension and slight shortening of the floss strand.

From the description heretofore, it will be appreciated that the apparatus disclosed causes the coil previously wound on a mandrel 153 to be captured between lower packaging film strip 171 and upper packaging film strip 172 and transported to the next stage of the process in which it is operated on by heat sealer 147 actuated by heat sealer actuator 143. In the case of floss coils with a nominal diameter of one inch, it is found convenient to have the traverse of the coils between successive mandrel positions determined at about two inches and the width of the packaging film strip 171 and 172 to also be approximately two inches. With this arrangement, the heat sealer 147 may be designed to produce a substantially square seal between the lower film strip 171 and the upper packaging film strip 172 effectively encapsulating the coil removed from a mandrel 153 while leaving intact the coil strand entering and leaving the capsule. The transverse dimensions of the peripheral heat seal may be from one and one-half to one and three-quarters inches.

After the continuous length of encapsulated coils of floss strand exits the rolls 173 and 174 of the film feed 165, the strip may be wound on a large supply coil for further processing or it may be cut into individual packages approximately two inches by two inches as a part of the same operation.

Figure 12:
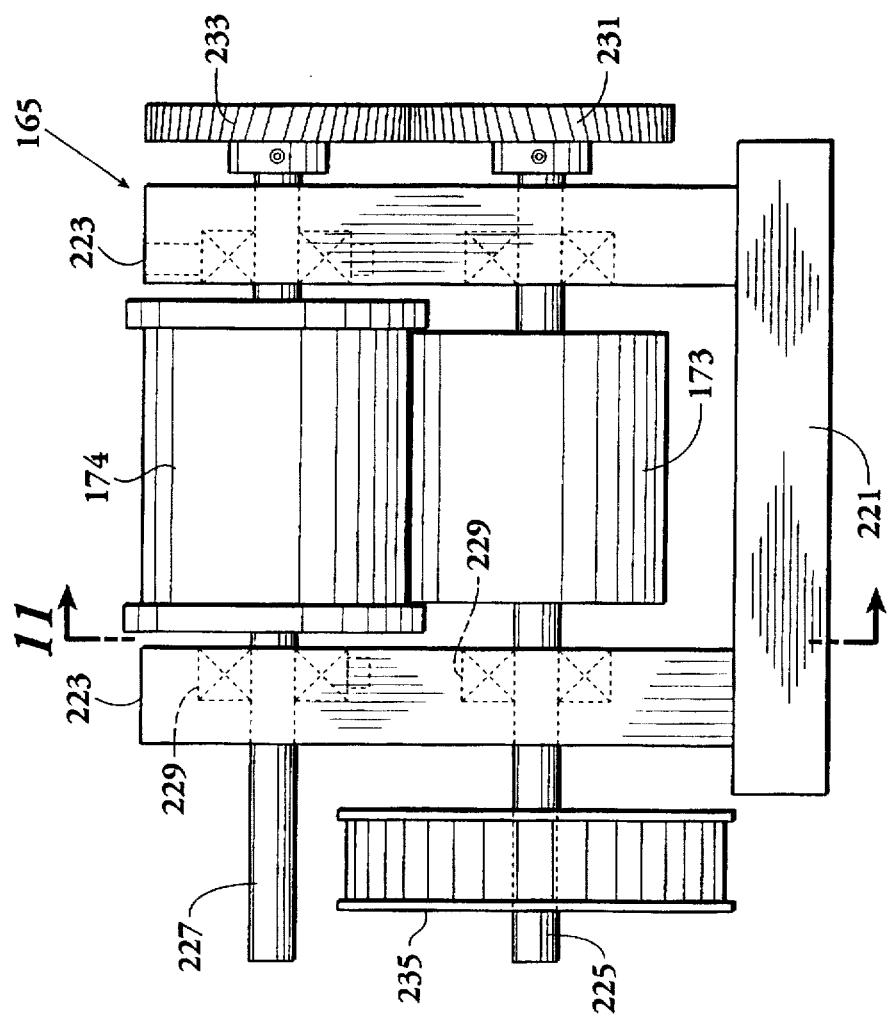
FIG. 12 is a front elevational view of the apparatus of FIG. 11.
Figure 11:
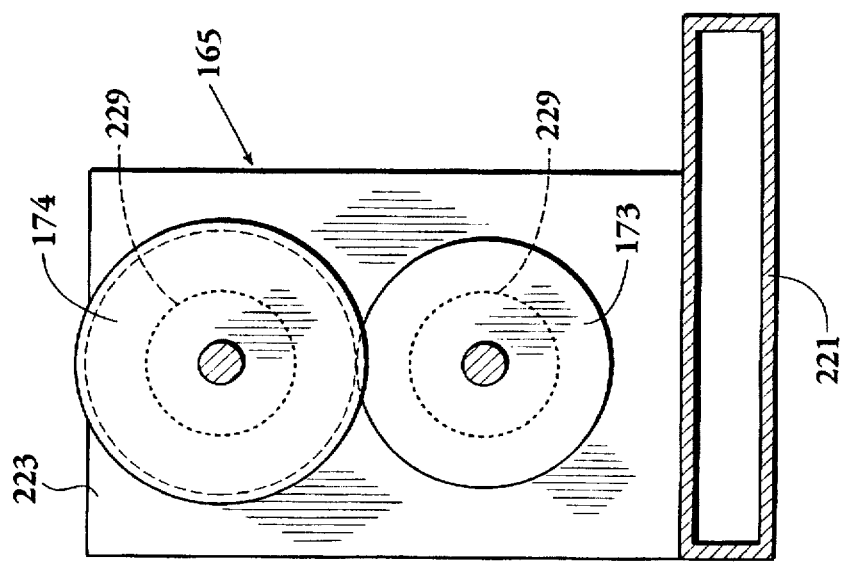
FIG. 11 is a detailed side elevational view of film feed apparatus of FIG. 9.

The film feed apparatus is shown in somewhat more detail in FIGS. 11 and 12 where rolls 173 and 174 are shown rotatably mounted on a base 221 having uprights 223 supporting shafts 225 and 227. Rolls 173 and 174 are fixedly mounted on shafts 225 and 227, respectively, and shafts 225 and 227 are provided with low friction bearings 229.

Rolls 173 and 174 are coupled to rotate at the same speed by gears 231 and 233 and a toothed belt pulley 235 on shaft 225 is driven directly or indirectly from stepper motor 163 in a conventional manner not illustrated in FIG. 12.

Figure 13:
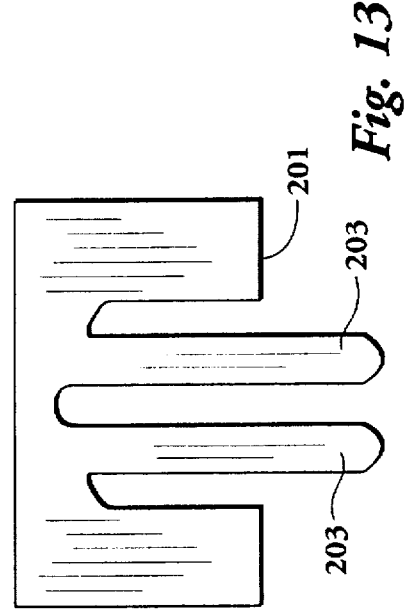
FIG. 13 is a plan view of the pick-off element of FIG. 8.
Figure 14:
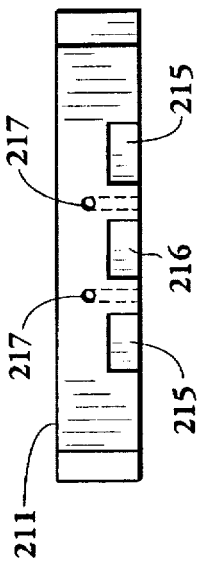
FIG. 14 is a front elevational view of the top plate associated with the pick-off element of FIG. 13.
Figure 15:
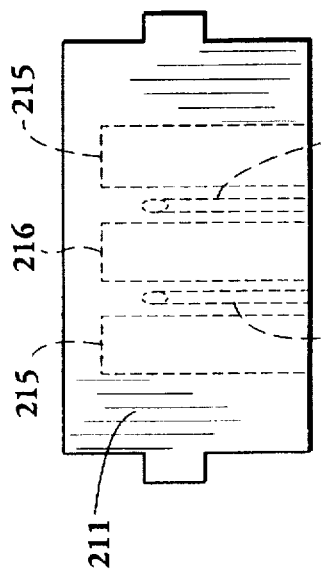
FIG. 15 is a top plan view of the top plate of FIG. 14.

FIGS. 13, 14, and 15 have been described in connection with the description of FIG. 8 and need not be referred to further.

In addition to the modifications and variations in the invention which have been described, shown, or suggested above, it will be apparent to those skilled in the art that other variations and modifications to the invention may be effected and, accordingly, the scope of the invention is not to be considered limited to those described, shown, or suggested above.

What is claimed is:

1. A process of making a series of coils of strand material in an individual dental floss segment packaging process comprising the steps of:
   (A) supplying a strand material to a rotating guide element;
   (B) placing a first mandrel having a transverse dimension of at least one-half inch inside a path of rotation of said guide element;
   (C) rotating said guide element at least three rotations to cause turns of said strand to be wound on said first mandrel;
   (D) removing said first mandrel and the strands wound thereon from said path of rotation;
   (E) placing a second mandrel inside said path of rotation;
   (F) causing said strand portion wound on said first mandrel to be removed therefrom while retaining a coil shape imparted by said first mandrel;
   (G) repeating step (B) and subsequent steps substituting said second mandrel for said first mandrel and substituting a third mandrel for said second mandrel to produce a series of coils formed of said strand material.

2. A process as recited in claim 1 further including the step of transporting said strand portion removed from said first mandrel to a subsequent packaging stage position.

3. A process as recited in claim 1 wherein said step of causing said strand portion wound on said first mandrel to be removed includes positioning a pick-off element in an opening through said first mandrel below the turns wound on said mandrel and lowering said mandrel to leave said coil resting on said pick-off element.

4. A process as recited in claim 1 wherein the step of removing said first mandrel from said path of rotation is effected by rotating a mounting element for all mandrels including said first mandrel by at least 10° and no more than 90°.

5. A process as recited in claim 4 wherein said step of removing said first mandrel from said path of rotation is carried out in a time less than the time for one rotation of said rotating guide element.

6. A process as recited in claim 1 wherein said step of supplying a strand material to a rotating guide element includes passing a strand of said material through a hollow shaft for said rotating guide element.

7. A process as recited in claim 1 wherein said step of removing said first mandrel from said path of rotation is carried out in a time less than the time for one rotation of said rotating guide element.

8. A process of making a series of coils of flexible strand material in an individual dental floss segment packaging process comprising the steps of:
   (A) supplying a strand material to a rotating guide element;
   (B) placing a first mandrel having a transverse dimension of less than about three inches inside a path of rotation of said guide element;
   (C) rotating said guide element from three to twelve rotations to cause turns of said strand to be wound on said first mandrel;
   (D) removing said first mandrel and the strands wound thereon from said path of rotation;
   (E) placing a second mandrel inside said path of rotation;
   (F) causing said strand portion wound on said first mandrel to be removed therefrom while retaining a coil shape imparted by said first mandrel; and
   (G) repeating step (B) and subsequent steps substituting said second mandrel for said first mandrel and substituting a third mandrel for said second mandrel to produce a series of interconnected coils formed of said strand material supplied to said rotating guide element.

9. A process as recited in claim 8 further including the step of transporting said strand portion removed from said first mandrel to a subsequent packaging stage position.

10. A process as recited in claim 8 wherein said step of causing said strand portion wound on said first mandrel to be removed includes positioning a pick-off element in an opening through said first mandrel below the turns wound on said mandrel and lowering said mandrel to leave said coil resting on said pick-off element.

11. A process as recited in claim 8 wherein the step of removing said first mandrel from said path of rotation is effected by rotating a mounting element for said first mandrel and other mandrels by at least 10°.

12. A process as recited in claim 11 wherein said step of removing said first mandrel from said path of rotation is carried out in a time less than the time for one rotation of said rotating guide element.

13. A process as recited in claim 8 wherein said step of supplying a strand material to a rotating guide element includes passing a strand of said material through a hollow shaft for said rotating guide element.

14. In an individual dental floss segment packaging machine, apparatus for making a series of coils of dental floss strand material comprising:

(A) a rotatable guide element;

(B) means for feeding a strand material to said rotatable guide element;

(C) a circular array of at least three mandrels;

(D) means for positioning one of said mandrels inside a path of rotation of said guide element;

(E) means for counting guide element rotations while turns of said strand are wound on said one of said mandrels;

(F) means for advancing said array to move said one of said mandrels and the strands wound thereon from within said path of rotation and moving an other one of said mandrels inside said path of rotation;

(G) means for causing said strand portion wound on said one of said mandrels to be removed therefrom while retaining a coil shape;

(H) control means for sequentially advancing said array of mandrels and causing removal of said coil-shaped strands to produce a series of coils of strand material.

15. Apparatus as recited in claim 14 further including means for transporting each strand portion removed from one of said mandrels to a subsequent packaging stage position.

16. Apparatus as recited in claim 14 wherein said rotatable guide element is mounted on a hollow shaft and said means for feeding a strand material to said rotatable guide element includes means for guiding said strand material through said hollow shaft of said rotatable guide element.

17. Apparatus for making a series of packages enclosing individual coils of strand material comprising:

(A) a supply roll of strand material;

(B) a rotatable guide mounted on a hollow shaft; said roll of strand material being positioned to feed a strand of said strand material to said rotatable guide;

(C) a circular array of at least three mandrels;

(D) means for positioning a selected one of said mandrels inside a path of rotation of said guide;

(E) means for rotating said guide and counting guide rotations while turns of said strand are wound on a first selected one of said mandrels;

(F) means for advancing said array to move said first selected one of said mandrels and the strands wound thereon from inside said path of rotation and moving a second selected one of said mandrels inside said path of rotation;

(G) means for causing said strand portion wound on said first selected one of said mandrels to be removed therefrom while retaining a coil shape;

(H) means for supplying upper and lower elongated packaging film strips and for guiding said strips to near proximity at a circumferential position of said circular array of mandrels;

(I) means for causing a just removed coil shaped strand portion to be captured between said upper and lower elongated packaging film strips;

(J) means for making a peripheral seal around said coil shaped strand portion; and (K) control means for sequentially advancing said array of mandrels, causing removal of said coil shaped strands, capturing said coil shaped strands between said film strips, advancing said film strips, and making a seal therein to produce a series of packages enclosing individual coils of strand material.

18. Apparatus as recited in claim 17 wherein said means for causing said strand portion wound on said first mandrel to be removed includes a pick-off element insertable in an opening through said first mandrel below the turns wound on said mandrel and means for lowering said mandrel to leave a coil formed by said turns on said pick-off element.

19. Apparatus as recited in claim 17 wherein said means for advancing said array to remove said first selected one of said mandrels from inside said rotatable guide path of rotation operates in a time equal to or less than the time for about one rotation of said rotatable guide.

20. Apparatus as recited in claim 17 wherein said means for causing a just removed coil-shaped strand portion to be captured between said upper and lower elongated packaging film strips includes means for producing an air jet aimed to urge said just removed coil from a position above a lowered mandrel to within the space between said elongated packaging film strips in near proximity.

* * * * *

UNITED STATES PATENT AND TRADEMARK OFFICE
CERTIFICATE OF CORRECTION

PATENT NO. : 5,765,343
DATED : June 16, 1998
INVENTOR(S) : Dale Whittaker

It is certified that error appears in the above-identified patent and that said Letters Patent is hereby corrected as shown below:

Col. 5, line 57, delete "example" and substitute --example,-- therefor;
       line 60, delete "inches center" and substitute --inches. Center-- therefor.

Signed and Sealed this

Thirteenth Day of October 1998

Attest:

BRUCE LEHMAN

Attesting Officer

Commissioner of Patents and Trademarks